(12) United States Patent
Olsen et al.

(10) Patent No.: US 6,413,737 B1
(45) Date of Patent: Jul. 2, 2002

(54) ECARIN PROTHROMBIN PROTEASE AND METHODS

(75) Inventors: David R. Olsen, Menlo Park; Jeff Prior; Louis C. Sehl, both of Redwood City; Donald G. Wallace, Menlo Park, all of CA (US)

(73) Assignee: Cohesion Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/608,790

(22) Filed: Jun. 30, 2000

Related U.S. Application Data
(60) Provisional application No. 60/143,128, filed on Jul. 9, 1999.

(51) Int. Cl.$^7$ .......................... C12P 21/06; C12N 9/48; C12N 9/74
(52) U.S. Cl. ...................... 435/68.1; 435/212; 435/226; 435/214
(58) Field of Search .................................. 435/226, 68.1, 435/212, 214

(56) References Cited

PUBLICATIONS

Nishida et al. (1995) Biochemistry 34(5):1771–8.*

* cited by examiner

*Primary Examiner*—Rebecca E. Prouty
*Assistant Examiner*—David J. Steadman
(74) *Attorney, Agent, or Firm*—Richard Aron Osman

(57) ABSTRACT

New forms of ecarin, a procoagulant protein from *Echis carinatus* venom, are described, as are polynucleotides encoding the new proteins, methods for production of the new proteins, and methods for activation of prothrombin using the new proteins. The new ecarins comprise a serine at position 396 of the protein. The new proteins may be used for activation of prothrombin, and are particularly useful for the production of recombinant thrombin.

28 Claims, 8 Drawing Sheets

FIG. 1

```
  +1                                                              60
    MIQILLVIICLAVFPYQGCSIILGSGNVNDYEVVYPQKVTALPKGAVQQPEQKYEDAMQY 61                                                             120
    EFEVKGEPVVLHLEKNKELFSEDYSETHYSSDDREITTNPSVEDHCYYHGRIQNDAESTA 121                                                             180
    SISACNGLKGHFKLRGETYFIEPLKIPDSEAHAVYKYENIENEDEAPKMCGVTQDNWESD 181                                                             240
    EPIKKTLGLIVPPHERKFEKKFIELVVVVDHSMVTKYNNDSTAIRTWIYEMLNTVNEIYL 241                                                             300
    PFNIRVALVGLEFWCNGDLINVTSTADDTLHSFGEWRASDLLNRKRHDHAQLLTNVTLDH 301                                                             360
    STLGITFVYGMCKSDRSVELILDYSNITFNMAYIIAHEMGHSLGMLHDTKFCTCGAKPCI 361                                                             420
    MFGKESIPPPKEFSSCSYDQYNKYLLKYNPKCILDSPLRKDIASPAVCGNEIWEEGEECD 421                                                             480
    CGSPADCRNPCCDAATCKLKPGAECGNGECCDKCKIRKAGTECRPARDDCDVAEHCTGQS 481                                                             540
    AECPRNEFQRNGQPCLNNSGYCYNGDCPIMLNQCIALFSPSATVAQDSCFQRNLQGSYYG 541                                                             600
    YCTKEIGYYGKRFPCAPQDVKCGRLYCLDNSFKKNMRCKNDYSYADENKGIVEPGTKCED 601              616
    GKVCINRKCVDVNTAY*    (SEQ ID NO:1)
```

FIG. 2A

```
1                                                           60
atgatccagattctcttggtaattatatgcttagcagttttccatatcaaggttgctct 61                                                          120
ataatcctgggatctgggaatgttaatgattatgaagtagtgtatccacaaaaagtcact 121                                                         180
gcattgcccaaaggagcagttcagcagcctgagcaaaagtatgaagatgccatgcaatat 181                                                         240
gaatttgaagtgaagggagagccagtggtccttcacctagaaaaaaataaagaactttt 241                                                         300
tcagaagattacagtgagactcattattcgtctgatgacagagaaattacaacaaaccct 301                                                         360
tcagttgaggatcactgctattatcatggacggatccagaatgatgctgagtcaactgca 361                                                         420
agcatcagtgcatgcaatggtttgaaaggacatttcaagcttcgaggggagacgtacttt 421                                                         480
attgaaccttgaagattcccgacagtgaagcccatgcagtctacaaatatgaaaacata 481                                                         540
gaaaatgaggatgaagcccccaaaatgtgtggggtaacccaggataattgggaatcagat 541                                                         600
gaacccatcaaaaagactttggggttaattgttcctcctcatgaacgaaaatttgagaaa 601                                                         660
aaattcattgagcttgtcgtagttgtggaccacagtatggtcacaaaatacaacaatgat 661                                                         720
tcaactgctataagaacatggatatatgaaatgctcaacactgtaaatgagatatactta 721                                                         780
cctttcaatattcgtgtagcactggttggcctagaatttggtgcaatggagacttgatt 781                                                         840
aacgtgacatccacagcagatgatactttgcactcatttggagaatggagagcatcagat 841                                                         900
ttgctgaatcgaaaagacatgatcatgctcagttactcacgaacgtgacactggatcat 901                                                         960
tccactcttggaatcacgttcgtatatggcatgtgcaaatcagatcgttctgtagaactt
```

FIG. 2B 961                                                                          1020
attctggattacagcaacataacttttaatatggcatatataatagcccatgagatgggt 1021                                                                         1080
catagtctgggcatgttacatgacacaaaattctgtacttgtggggctaaaccatgcatt 1081                                                                         1140
atgtttggcaaagaaagcattccaccgcccaaagaattcagcagttgtagttatgaccag 1141                                                                         1200
tataacaagtatcttcttaaatataacccaaaatgcattcttgattccctttgagaaaa 1201                                                                         1260
gatattgcttcacctgcagtttgtggaaatgaaatttgggaggaaggagaagaatgtgat 1261                                                                         1320
tgtggttctcctgcagattgtcgaaatccatgctgtgatgctgcaacatgtaaactgaaa 1321                                                                         1380
ccaggggcagaatgtggaaatggagagtgttgtgacaagtgcaagattaggaaagcagga 1381                                                                         1440
acagaatgccggccagcaagggatgactgtgatgtcgctgaacactgcactggccaatct 1441                                                                         1500
gctgagtgtcccagaaatgagttccaaaggaatggacaaccatgccttaacaactcgggt 1501                                                                         1560
tattgctacaatggggattgccccatcatgttaaaccaatgtattgctctctttagtcca 1561                                                                         1620
agtgcaactgtggctcaagattcatgttttcagaggaacttgcaaggcagttactatggc 1621                                                                         1680
tactgcacaaaggaaattggttactatggtaaaaggtttccatgtgcaccacaagatgta 1681                                                                         1740
aaatgtggcagattatactgcttagataattcattcaaaaaaaatatgcgttgcaagaac 1741                                                                         1800
gactattcatacgcggatgaaaataagggaatagttgaacctggaacaaaatgtgaagat 1801                                                       1851
ggaaaggtctgcatcaacaggaagtgtgttgatgtgaatacagcctactaa (SEQ ID NO:2)

SEQUENCE LISTING

<160> NUMBER OF SEQ ID NOS: 6

<210> SEQ ID NO 1
<211> LENGTH: 616
<212> TYPE: PRT
<213> ORGANISM: E. carinatus leucogaster

<400> SEQUENCE: 1

```
Met Ile Gln Ile Leu Leu Val Ile Ile Cys Leu Ala Val Phe Pro Tyr
 1               5                  10                  15

Gln Gly Cys Ser Ile Ile Leu Gly Ser Gly Asn Val Asn Asp Tyr Glu
            20                  25                  30

Val Val Tyr Pro Gln Lys Val Thr Ala Leu Pro Lys Gly Ala Val Gln
        35                  40                  45

Gln Pro Glu Gln Lys Tyr Glu Asp Ala Met Gln Tyr Glu Phe Glu Val
    50                  55                  60

Lys Gly Glu Pro Val Val Leu His Leu Glu Lys Asn Lys Glu Leu Phe
65                  70                  75                  80

Ser Glu Asp Tyr Ser Glu Thr His Tyr Ser Ser Asp Asp Arg Glu Ile
                85                  90                  95
```

```
Thr Thr Asn Pro Ser Val Glu Asp His Cys Tyr Tyr His Gly Arg Ile
            100                 105                 110

Gln Asn Asp Ala Glu Ser Thr Ala Ser Ile Ser Ala Cys Asn Gly Leu
            115                 120                 125

Lys Gly His Phe Lys Leu Arg Gly Glu Thr Tyr Phe Ile Glu Pro Leu
            130                 135                 140

Lys Ile Pro Asp Ser Glu Ala His Ala Val Tyr Lys Tyr Glu Asn Ile
145                 150                 155                 160

Glu Asn Glu Asp Glu Ala Pro Lys Met Cys Gly Val Thr Gln Asp Asn
                165                 170                 175

Trp Glu Ser Asp Glu Pro Ile Lys Lys Thr Leu Gly Leu Ile Val Pro
                180                 185                 190

Pro His Glu Arg Lys Phe Glu Lys Lys Phe Ile Glu Leu Val Val Val
            195                 200                 205

Val Asp His Ser Met Val Thr Lys Tyr Asn Asn Asp Ser Thr Ala Ile
            210                 215                 220

Arg Thr Trp Ile Tyr Glu Met Leu Asn Thr Val Asn Glu Ile Tyr Leu
225                 230                 235                 240

Pro Phe Asn Ile Arg Val Ala Leu Val Gly Leu Glu Phe Trp Cys Asn
                245                 250                 255

Gly Asp Leu Ile Asn Val Thr Ser Thr Ala Asp Asp Thr Leu His Ser
            260                 265                 270

Phe Gly Glu Trp Arg Ala Ser Asp Leu Leu Asn Arg Lys Arg His Asp
            275                 280                 285

His Ala Gln Leu Leu Thr Asn Val Thr Leu Asp His Ser Thr Leu Gly
            290                 295                 300

Ile Thr Phe Val Tyr Gly Met Cys Lys Ser Asp Arg Ser Val Glu Leu
305                 310                 315                 320

Ile Leu Asp Tyr Ser Asn Ile Thr Phe Asn Met Ala Tyr Ile Ile Ala
                325                 330                 335

His Glu Met Gly His Ser Leu Gly Met Leu His Asp Thr Lys Phe Cys
            340                 345                 350

Thr Cys Gly Ala Lys Pro Cys Ile Met Phe Gly Lys Glu Ser Ile Pro
            355                 360                 365

Pro Pro Lys Glu Phe Ser Ser Cys Ser Tyr Asp Gln Tyr Asn Lys Tyr
            370                 375                 380

Leu Leu Lys Tyr Asn Pro Lys Cys Ile Leu Asp Ser Pro Leu Arg Lys
385                 390                 395                 400

Asp Ile Ala Ser Pro Ala Val Cys Gly Asn Glu Ile Trp Glu Glu Gly
                405                 410                 415

Glu Glu Cys Asp Cys Gly Ser Pro Ala Asp Cys Arg Asn Pro Cys Cys
            420                 425                 430

Asp Ala Ala Thr Cys Lys Leu Lys Pro Gly Ala Glu Cys Gly Asn Gly
            435                 440                 445

Glu Cys Cys Asp Lys Cys Lys Ile Arg Lys Ala Gly Thr Glu Cys Arg
450                 455                 460

Pro Ala Arg Asp Asp Cys Asp Val Ala Glu His Cys Thr Gly Gln Ser
465                 470                 475                 480

Ala Glu Cys Pro Arg Asn Glu Phe Gln Arg Asn Gly Gln Pro Cys Leu
            485                 490                 495

Asn Asn Ser Gly Tyr Cys Tyr Asn Gly Asp Cys Pro Ile Met Leu Asn
            500                 505                 510
```

-continued

```
Gln Cys Ile Ala Leu Phe Ser Pro Ser Ala Thr Val Ala Gln Asp Ser
                515                 520                 525
Cys Phe Gln Arg Asn Leu Gln Gly Ser Tyr Tyr Gly Tyr Cys Thr Lys
        530                 535                 540
Glu Ile Gly Tyr Tyr Gly Lys Arg Phe Pro Cys Ala Pro Gln Asp Val
545                 550                 555                 560
Lys Cys Gly Arg Leu Tyr Cys Leu Asp Asn Ser Phe Lys Lys Asn Met
                565                 570                 575
Arg Cys Lys Asn Asp Tyr Ser Tyr Ala Asp Glu Asn Lys Gly Ile Val
            580                 585                 590
Glu Pro Gly Thr Lys Cys Glu Asp Gly Lys Val Cys Ile Asn Arg Lys
        595                 600                 605
Cys Val Asp Val Asn Thr Ala Tyr
    610                 615

<210> SEQ ID NO 2
<211> LENGTH: 1851
<212> TYPE: DNA
<213> ORGANISM: E. carinatus leucogaster

<400> SEQUENCE: 2
atgatccaga ttctcttggt aattatatgc ttagcagttt ttccatatca aggttgctct      60
ataatcctgg gatctgggaa tgttaatgat tatgaagtag tgtatccaca aaaagtcact     120
gcattgccca aggagcagtt tcagcagcct gagcaaaagt atgaagatgc catgcaatat     180
gaatttgaag tgaagggaga gccagtggtc cttcacctag aaaaaaataa agaactttt     240 tcagaagatt acagtgagac tcattattcg tctgatgaca gagaaattac aacaaaccct     300
tcagttgagg atcactgcta ttatcatgga cggatccaga atgatgctga gtcaactgca     360
agcatcagtg catgcaatgg tttgaaagga catttcaagc ttcgagggga gacgtacttt     420
attgaaccct tgaagattcc cgacagtgaa gcccatgcag tctacaaata tgaaaacata     480
gaaaatgagg atgaagcccc caaatgtgt ggggtaaccc aggataattg gaatcagat      540 gaacccatca aaagactttt ggggttaatt gttcctcctc atgaacgaaa atttgagaaa     600
aaattcattg agcttgtcgt agttgtggac cacagtatgg tcacaaaata caacaatgat     660
tcaactgcta taagaacatg gatatatgaa atgctcaaca ctgtaaatga gatatactta     720
cctttcaata ttcgtgtagc actggttggc ctagaatttt ggtgcaatgg agacttgatt     780
aacgtgacat ccacagcaga tgatactttg cactcatttg agaatggag agcatcagat     840 ttgctgaatc gaaaaagaca tgatcatgct cagttactca cgaacgtgac actggatcat     900
tccactcttg gaatcacgtt cgtatatggc atgtgcaaat cagatcgttc tgtagaactt     960
attctggatt acagcaacat aacttttaat atggcatata aatagccca tgagatgggt    1020 catagtctgg gcatgttaca tgacacaaaa ttctgtactt gtggggctaa ccatgcatt    1080 atgtttggca agaaagcat tccaccgccc aaagaattca gcagttgtag ttatgaccag    1140
tataacaagt atcttcttaa atataaccca aaatgcattc ttgattcacc tttgagaaaa    1200
gatattgctt cacctgcagt ttgtggaaat gaaatttggg aggaaggaga agaatgtgat    1260
tgtggttctc ctgcagattg tcgaaatcca tgctgtgatg ctgcaacatg taaactgaaa    1320
ccaggggcag aatgtggaaa tggagagtgt tgtgacaagt gcaagattag gaaagcagga    1380
acagaatgcc ggccagcaag ggatgactgt gatgtcgctg aacactgcac tggccaatct    1440
gctgagtgtc ccagaaatga gttccaaagg aatggacaac catgccttaa caactcgggt    1500
```

-continued

```
tattgctaca atggggattg ccccatcatg ttaaaccaat gtattgctct ctttagtcca    1560
agtgcaactg tggctcaaga ttcatgtttt cagaggaact tgcaaggcag ttactatggc    1620
tactgcacaa aggaaattgg ttactatggt aaaaggtttc catgtgcacc acaagatgta    1680
aaatgtggca gattatactg cttagataat tcattcaaaa aaaatatgcg ttgcaagaac    1740
gactattcat acgcggatga aaataaggga atagttgaac ctggaacaaa atgtgaagat    1800
ggaaaggtct gcatcaacag gaagtgtgtt gatgtgaata cagcctacta a             1851
```

<210> SEQ ID NO 3
<211> LENGTH: 4
<212> TYPE: PRT
<213> ORGANISM: Unknown
<220> FEATURE:
<223> OTHER INFORMATION: This sequence is an ecarin recognition site.

<400> SEQUENCE: 3

Ile Asp Gly Arg
 1

<210> SEQ ID NO 4
<211> LENGTH: 4
<212> TYPE: PRT
<213> ORGANISM: Unknown
<220> FEATURE:
<223> OTHER INFORMATION: This sequence is an ecarin recognition site.

<400> SEQUENCE: 4

Asp Gly Arg Ile
 1

<210> SEQ ID NO 5
<211> LENGTH: 6
<212> TYPE: PRT
<213> ORGANISM: Unknown
<220> FEATURE:
<223> OTHER INFORMATION: This sequence is an ecarin recognition site.

<400> SEQUENCE: 5

Ile Asp Gly Arg Ile Val
 1               5

<210> SEQ ID NO 6
<211> LENGTH: 6
<212> TYPE: PRT
<213> ORGANISM: Unknown
<220> FEATURE:
<223> OTHER INFORMATION: This sequence is an ecarin recognition site.

<400> SEQUENCE: 6

Asp Gly Arg Ile Val Glu
 1               5

ECARIN PROTHROMBIN PROTEASE AND METHODS

CROSS-REFERENCE TO RELATED APPLICATION

This application claims priority to 60/143,128, by inventor David Olsen, entitled *Ecarin Polypeptides, Polynucleotides Encoding Ecarin, and Methods for Use Thereof*, filed Jul. 9, 1999, which is incorporated herein by reference.

TECHNICAL FIELD

The invention relates to the field of recombinant proteins, more particularly to new variants of the protease ecarin. The invention provides polynucleotides encoding the new ecarin polypeptides, the polypeptides themselves, and methods of using them.

BACKGROUND

A large number of enzymes, particularly proteases, with pathologic effects have been isolated from various snake venoms. Commonly, snake venoms contain procoagulants (e.g., factors which stimulate blood coagulation) and/or hemorrhagic agents (e.g., factors which break down the basement membrane of the vascular endothelium, causing internal bleeding; factors which inhibit platelet aggregation).

The complete amino acid sequences, and in some cases the nucleotide sequences encoding them, have been reported for a number of procoagulants and hemorrhagic agents found in venom from snakes of various genera, including Crotalus, Trimeresus, Lachesis (all of the family Crotalidae), Daboia (Russells' viper), and Echis (Iwanaga et al., 1993, in *Methods in Protein Sequence Analysis*, Imahori et al. eds., pp. 107–115, Plenum Press, London; Tokunaga et al., 1992, *J. Biol. Chem.* 267:14109–14117; Nishida et al., 1995, *Biochem.* 34:1771–1778).

The venom of *Echis carinatus* contains a procoagulant which may be of particular interest for certain segments of the biotechnology industry. The procoagulant, a protease named ecarin which activates prothrombin, is useful in assays of blood coagulation because it is relatively resistant to heparin and other therapeutic anticoagulants (Berry et al., 1998, *Thromb. Haemost.* 79(1):228–233). Ecarin cleaves human prothrombin between residues $Arg_{320}$-$Ile_{321}$ to generate meizothrombin. Autocatalytic processing results in the formation of meizothrombin desF1 and then α-thrombin, the mature, active form of thrombin (Rhee et al., 1982, *Biochemistry* 21:3437–3443).

Thrombin is a component of a number of hemostat/wound dressing products that are currently in use or in development. Such products generally incorporate active thrombin (e.g., α-thrombin) derived from animal blood, most commonly bovine blood. However, concerns regarding possible disease transmission (especially prion-transmitted diseases) have made animal blood a less attractive source of thrombin. Human blood derived thrombin is also undesirable due to the additional possibility of transmission of viral disease, such as AIDS, hepatitis B, hepatitis C, and the like. Recombinant human thrombin would greatly reduce the risk of disease transmission via thrombin-containing products, as well as the likelihood of adverse immune reactions upon repeat usage of thrombin-containing products. Recombinant thrombin, particularly human recombinant thrombin would, therefore, be a very desirable substitute for blood derived thrombin.

Thrombin is expressed as a "prepro" protein; that is, the protein is expressed including an amino terminal secretion signal sequence (the "pre"domain) as well as a domain which must be removed before the thrombin can be active (the "pro" domain). In vivo prothrombin processing or activation to thrombin is initiated by the formation of the prothrombinase enzyme complex. The prothrombinase complex consists of the enzyme, factor Xa, a cofactor, factor Va, and calcium ions all of which assemble on a phospholipid surface (normally provided by platelets or endothelial cells). Activation can proceed by two possible pathways (the first involves cleavage at Arg271-Thr272, the reaction products being intermediates called fragment 1.2 and prethrombin-2) The fully active prothrombinase complex activates Factor II by cleavage at Arg320-Ile321 yielding the intermediate meizothrombin). A second cleavage gives rise to α-thrombin. The complexity of the natural activation of prothrombin makes it unsuitable for the commercial manufacture of α-thrombin from recombinant prothrombin.

Accordingly, a need exists in the art for compositions and methods that allow the efficient in vitro processing of preprothrombin and prothrombin to active thrombin.

DISCLOSURE OF THE INVENTION

The inventor has found a new form of the enzyme ecarin which has a different sequence from the one known sequence for Kenyan *Echis carinatus* ecarin. The new ecarin was derived from *Echis carinatus leucogaster*, and differs from the known sequence of ecarin by a single amino acid residue. However, the difference between the two sequences is significant, as the alteration is in the catalytic domain of the protein, and involves a change from a proline (in the known sequence) to a serine (in the protein of the invention). Amino acid sequence changes involving proline are considered non-homologous changes, as proline can have drastic effects on secondary and higher protein structure, due to the particular chemical structure of proline.

In one aspect, the invention relates to polypeptides comprising the ecarin metalloprotease domain of SEQ ID NO:1, shown in FIG. 1, as well as polynucleotides encoding such proteins. Other polypeptides included within the invention comprise residues 17–616 and/or residues 290–616 of SEQ ID NO:1, shown in FIG. 1, as well as polynucleotides encoding the polypeptides. Additionally, the invention provides variants thereof, including variants wherein position 170 of the protein (SEQ ID NO:1) is altered from cysteine to another amino acid residue, such as serine.

In another aspect, the invention relates to methods for making mature thrombin, comprising treating prothrombin with active ecarin of the invention. The thrombin may be treated in vitro with the ecarin of the invention or during production by co-expression of genes encoding the ecarin of the invention and prothrombin in the same cell.

In a further aspect, the invention provides methods of cleaving proteins, such as genetically engineered fusion proteins, containing an ecarin recognition site. The site may be naturally occurring, or the protein may be engineered to contain an ecarin cleavage site.

BRIEF DESCRIPTION OF THE DRAWINGS

FIG. 1 shows the amino acid sequence (SEQ ID NO:1) of preproecarin of the invention.

FIGS. 2A and 2B show the *E. carinatus leucogaster* nucleotide sequence (SEQ ID NO:2) encoding the protein (SEQ ID NO:1).

BEST MODE FOR CARRYING OUT THE INVENTION

Figure 3:
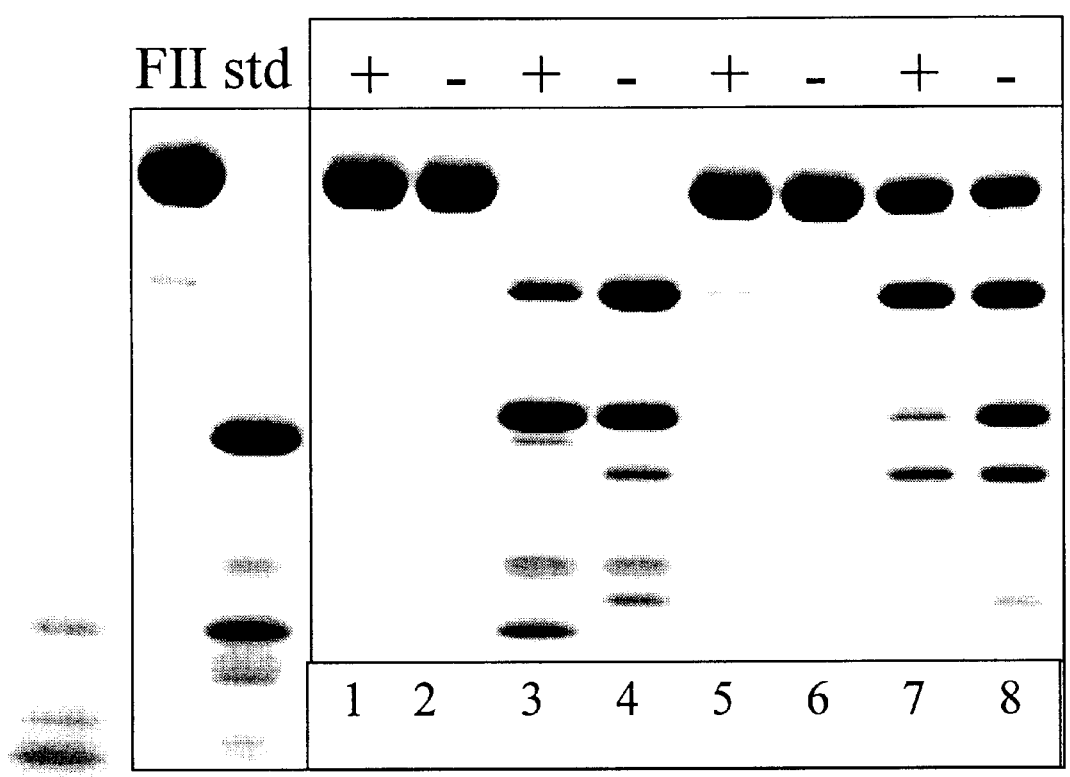
FIG. 3 shows SDS-PAGE analysis of purified prothrombin digested with various forms of proecarin of the invention before and after treatment with APMA (p-aminophenylmercuric acetate). FII indicates a purified prothrombin standard. "std" indicates prothrombin treated with venom-derived ecarin. 10 μg of purified prothrombin were incubated with conditioned medium from COS-7 cells transfected with pSG5 (backbone plasmid without insert; lanes 1–2), pDOEC30 (preproecarin of FIG. 1 (SEQ ID NO:1) with an added polyhistidine tag; lanes 3–4), pDOEC34 (ecarin of the sequence disclosed by Nishida et al., supra; lanes 5–6), or pDOEC35 (preproecarin of FIG. 1 (SEQ ID NO:1) with $Cys_{170}$ altered to serine). Conditioned medium was tested with (+) and without (−) preincubation with APMA. Protein bands were detected by staining with Coomassie blue.

The inventor has found a new form of ecarin, a procoagulant protein from *E. carinatus* venom. The new ecarin form was isolated from *E. carinatus leucogaster*, and differs from the known sequence for ecarin at a single, highly significant site. Position 396 of SEQ ID NO:1 (as shown in FIG. 1), is proline in the known sequence for ecarin and serine in the ecarin of the invention. This change is located within the catalytic domain of the protein, and represents a highly non-homologous substitution.

The invention provides full length ecarin (preproecarin), as well as proecarin (preproecarin less the secretion signal sequence) and mature ecarin (preproecarin less both the signal sequence and the pro domain). Additionally, the invention provides variant ecarins with alterations in the cysteine switch, such as preproecarin and proecarin having the sequence shown in FIG. 1 (SEQ ID NO:1) with a substitution at position 170, substituting another amino acid, such as serine, for the cysteine in the FIG. 1 sequence (SEQ ID NO:1).

The invention further provides methods of processing prothrombin, particularly recombinant prothrombin, with the ecarin of the invention to produce active thrombin. The treatment of the prothrombin may be in vitro, utilizing cell extracts, conditioned media, immobilized proteins, partially purified proteins, or purified proteins, or it may be in vivo as the product of recombinant expression of genes encoding the ecarin of the invention and prothrombin in the same cell.

Ecarin of the invention may also be used for proteolytic processing of fusion proteins, particularly recombinant fusion proteins which have been engineered to contain an ecarin recognition site.

Definitions

An "ecarin of the invention" is an ecarin polypeptide which has a serine in place of the previously disclosed proline at position 396 (or the homologue of position 396 in deletion or addition variants) of the protein. The amino acid sequence (SEQ ID NO:1) of a prototypic ecarin of the invention is shown in FIG. 1. An ecarin of the invention may additionally comprise further variations as compared to the previously disclosed sequence of ecarin, so long as the protein has a serine at position 396 of SEQ ID NO:1 (or the homolog of position 396) and retains prothrombin cleavage activity. Ecarin of the invention comprises four major domains, the prepro domain (residues 1–190 of SEQ ID NO:1, with a boundary between the pre and pro domains between residues 18 and 19 of SEQ ID NO:1 (FIG. 1)), the catalytic domain (residues 191–397 of SEQ ID NO:1 (FIG. 1)), the disintegrin domain (residues 398–490 of SEQ ID NO:1 (FIG. 1)) and the cysteine rich domain (residues 491–616 of SEQ ID NO:1 (FIG. 1)). Ecarin of the invention, in its active form and under the proper reaction conditions, has "ecarin activity" (i.e., the protein will process (cleave) prothrombin to produce meizothrombin).

Sequence "identity" and "homology", as referred to herein, can be determined using BLAST (Altschul, et al., 1990, *J. Mol. Biol.* 215(3):403–410), particularly BLASTP 2 as implemented by the National Center for Biotechnology Information (NCBI), using default parameters (e.g., Matrix 0 BLOSUM62, gap open and extension penalties of 11 and 1, respectively, gap x_dropoff 50 and wordsize 3). Unless referred to as "consecutive" amino acids, a sequence optionally can contain a reasonable number of gaps or insertions that improve alignment.

A "cysteine switch variant" ecarin is an ecarin of the invention which comprises an alteration in the "cysteine switch" of the prodomain (e.g., at position 170 and/or at positions surrounding position 170 of the sequence shown FIG. 1 (SEQ ID NO:1)). Where a cysteine switch variant ecarin of the invention differs from the amino acid sequence shown in FIG. 1 (SEQ ID NO:1) at sites other than the cysteine switch region, a cysteine switch variant will have alterations at positions homolgous to position 170 and/or positions surrounding position 170 of the sequence shown in FIG. 1 (SEQ ID NO:1).

A "heterologous activation variant" ecarin is an ecarin of the invention which has been engineered to contain the recognition and cleavage site of a protease which does not normally cleave proecarin, such as KEX2, human rhinovirus 3C protease, and the like. Preferably the heterologous cleavage site is located at or near the junction of the pro and catalytic domains of the protein.

"Ecarin activity" may be easily measured using any protocol known in the art for prothrombin activation by ecarin. Generally, prothrombin is contacted with activated ecarin (which may be a cysteine switch variant or ecarin activated by proteolytic cleavage of the prodomain or chemical treatment, such as with APMA) under appropriate conditions (for example, pH about 7–8.5, 0.1 M NaCl, 0.2% PEG1000). The resulting product is assayed for mature thrombin by any convenient assay, such as a chromogenic synthetic substrate assay, a clotting assay, or a western blotting assay using an anti-thrombin antibody for detection.

The term "isolated", as used herein, generally refers to a material which has been substantially purified from other materials found in its normal milieu.

For example, an "isolated ecarin of the invention" is ecarin which has been substantially purified or produced such that less than 10%, more preferably 5%, more preferably 1% of the non-ecarin proteins normally associated with ecarin in E. carinatus venom are present. The term "non-ecarin proteins" explicitly excludes the "pro" domain of ecarin. An "isolated polynucleotide" is one which is isolated from DNA sequences, particularly DNA sequences encoding structural genes (e.g., encoding proteins or structural RNAs), which normally flank the polynucleotide in the E. carinatus genome. DNA sequences which normally flank a DNA sequence encoding ecarin which are "control" sequences (e.g., promoters, enhancers, polyadenylation signals and the like) need not be removed for a polynucleotide to be considered "isolated".

The term "ecarin recognition site" refers to a polypeptide sequence which is recognized and cleaved by ecarin. Ecarin cleaves proteins and peptides after the sequence Asp-Gly-Arg or Glu-Gly-Arg, although longer recognition sites are preferred. Longer recognition sites can include, for example, the flanking sequences found in human prothrombin. Ecarin cleaves after the sequence Asp-Gly-Arg in human prothrombin (positions 361–363 of human preprothrombin, Genbank accession no. P00734), so sequences flanking this site may be included in an ecarin recognition site. For example, such recognition sites include He-Asp-Gly-Arg (SEQ ID NO:3), Asp-Gly-Arg-Ile (SEQ ID NO:4), Ile-Asp-Gly-Arg-Re-Val (SEQ ID NO:5), Asp-Gly-Arg-Ile-Val-Glu (SEQ ID NO:6), and the like. This recognition site is the only known cleavage site for ecarin, although a second site in prothrombin has been reported to be cleaved at a slower rate by an impure ecarin preparation (Briet et al., 1982, *Thrombosis Res.* 27:591–600). Cleavage at the second site may be due to impurities in the ecarin preparation.

The term "comprising" and its cognates (e.g., comprises, comprise, etc.), as used herein, are used in their inclusive sense (i.e., synonymous with "including and its corresponding cognates).

Methods for making the proteins and nucleotides of the invention, as well as the methods of the invention taught in this disclosure utilize the conventional techniques of molecular genetics, cell biology, and biochemistry. Useful methods in molecular genetics, cell biology and biochemistry are described in "Molecular Cloning: A Laboratory Manual", 2nd Ed. (Sambrook et al., 1989); "Oligonucleotide Synthesis" (M. J. Gait, ed., 1984); "Animal Cell Culture" (R. I. Freshney, ed., 1987); the series "Methods in Enzymology" (Academic Press, Inc.); "Gene Transfer Vectors for Mammalian Cells" (J. M. Miller & M. P. Calos, eds., 1987); "Current Protocols in Molecular Biology" and "Short Protocols in Molecular Biology, 3rd Edition" (F. M. Ausubel et al., eds., 1987 & 1995); and "Recombinant DNA Methodology II" (R. Wu ed., Academic Press 1995). Methods for peptide synthesis and manipulation are described in "Solid Phase Peptide Synthesis", (J. M. Stewart & J. D. Young, 1984); "Solid Phase Peptide Synthesis: A Practical Approach" (E. Atherton & R. C. Sheppard, 1989); "The Chemical Synthesis of Peptides" (J. Jones, International Series of Monographs on Chemistry vol. 23, 1991); and "Solid Phase Peptide Synthesis", (G. Barany & R. B. Merrifield, Chapter 1 of "The Peptides", 1979); and "Bioconjugate Techniques" (G. T. Hermanson, 1996).

FIG. 1 shows an exemplary ecarin sequence of the invention, SEQ ID NO:1. The invention also encompasses variants of the amino acid sequence disclosed in FIG. 1 (SEQ ID NO:1), as long as they include a serine at a location homologous to position 396 of FIG. 1 (SEQ ID NO:1). Additional ecarin polypeptides of the invention comprise an amino acid sequence that is identical or homologous to the amino acid sequence shown in FIG. 1 (SEQ ID NO:1). The identical or homologous sequence generally comprises the active domain of the protein (e.g., residues 191 through 397 of FIG. 1 (SEQ ID NO:1) and may contain further sequences if desired. The degree of identity in the region being compared between the sequences is typically at least 65%, 80%, 90%, 95%, 99% or 100% in order of increasing preference. Alternately, the degree of homology in the region being compared between the sequences is typically at least 85%, 90%, 95%, 99% or 100% in order of increasing preference.

Certain preferred embodiments include mature ecarin of the invention (e.g., amino acids 191–616 of SEQ ID NO:1 (FIG. 1)), proecarin of the invention (e.g., amino acids 19–616 of SEQ ID NO:1 (FIG. 1), as well as sequences having at least 65%, 80%, 90%, 95% or 99% identity to or 85%, 90%, 95% or 99% homology to the sequence of FIG. 1 (SEQ ID NO:1).

Another exemplary ecarin is an ecarin of the invention which further has alterations to make the protein constituitively active. One class of such constituitively active ecarins are those in which the "cysteine switch" consensus sequence of the protein has been altered to render the cysteine switch inoperative. The cysteine switch may be rendered inoperative by, for example, altering the cysteine residue at position 170 of FIG. 1 (SEQ ID NO:1) to a different amino acid. In one preferred ecarin of the invention, the cysteine at position 170 is altered to serine. Other "cysteine switch variants" include ecarin variants having serine at position 396 and an alteration in one or more amino acids flanking position 170 that alter the conformation and/or local environment of the cysteine at position 170 such that it can no longer function as a cysteine switch. Such alterations include: changing one or both of the amino acids flanking position 170 (i.e., positions 169 and/or 171) to bulky amino acids (e.g., phenylalanine, tyrosine) to sterically hinder the cysteine at position 170 from performing as a cysteine switch; changing one or more amino acids in the region near position 170 to alter charge (e.g., changing the lysine at position 168 to a glutamate residue) to block operation of the cysteine switch, altering one or more amino acids near position 170 (e.g., 165, 166, 168, 169, and/or 171–175) to a positionally constrained amino acid (e.g., proline); altering the proline at position 167 to a different amino acid, such as a serine; and any combination thereof.

Further variant ecarins of the invention include ecarins which have been modified to permit processing of ecarin to produce mature ecarin with a heterologous protease (e.g., a protease that does not normally cleave ecarin). In these "heterologous activation variants", a protease recognition sequence and cleavage site is inserted into the sequence of ecarin. For example, KEX2 is a well known yeast proteolytic enzyme. A KEX2 recognition site (Arg-Arg or Lys-Arg) may be introduced at residues 184–185 of SEQ ID NO:1 by making a conservative amino acid substitution from Lys-Lys to Lys-Arg or Arg-Arg or at residue 196–197 of SEQ ID NO:1 by substituting an Arg for Lys at position 197, permitting cleavage/activation of the recombinant protein by KEX2. Alternatively recognition sequences for other proteases such as furin/PACE, the mammalian homologue of KEX2, enterokinase, renin, thrombin, or viral protease 3C, or the like.

The proteins of the invention are generally isolated from non-ecarin proteins found in *E. carinatus* venom. Preferably, the proteins of the invention are produced by recombinant means, which results in ecarin which is free of non-ecarin proteins found in *E. carinatus* venom. However, certain embodiments of the invention, particularly cysteine switch variants and heterologous activation variants, need not be isolated.

The invention also encompasses polynucleotides encoding the various ecarins of the invention. In the case of *E. carinatus leucogaster* ecarin, the polynucleotides are generally isolated from sequences which naturally accompany the *E. carinatus leucogaster* gene in situ. Polynucleotides encoding variant ecarin need not be isolated, but may be isolated if that is desirable.

FIG. 2 shows the *E. carinatus leucogaster* nucleotide sequence encoding an ecarin of the invention. However, as will be apparent to one of skill in the art, the invention includes any nucleotide sequence encoding an ecarin protein of the invention. Accordingly, the nucleotide sequences of the invention may contain "silent mutations" which affect the nucleotide sequence but do not alter the encoded amino acid sequence. In certain embodiments, the polynucleotide encoding an ecarin of the invention is "codon optiized" (i.e., adjusted to account for codon preference) for a particular host cell. Such codon optimization is well known in the art (see, for example, Kim et al., 1997, *Gene* 199:293–301), and as described in U.S. Pat. No. 4,571,421 to Itakura.

Ecarin of the invention is preferably produced by recombinant means. Recombinant expression generally involves the creation of an "expression construct" which contains DNA encoding an ecarin of the invention (an "ecarin gene"), "operably linked" to other sequences necessary for expression of the ecarin gene ("control elements"). Operable linkage between an ecarin gene and a control element requires that the two sequences be in proper orientation and in sufficient proximity for the control sequences to be active. The details of an operable linkage between sequence elements will vary according to the exact identity and properties of the sequences, as will be apparent to one of skill in the art. The expression construct is transferred into a host cell, which is cultured and, if necessary, manipulated to induce expression of the ecarin of the invention.

The exact details of the expression construct will vary according to the particular host cell that is to be used as well as to the desired characteristics of the expression system, as is well known in the art. For example, for production in *S. cerevisiae*, the DNA encoding an ecarin of the invention is placed into operable linkage with a promoter that is operable in *S. cerevisiae* and which has the desired characteristics (e.g., inducible/derepressible or constituitive), such as GAL1–10, PHO5, PGK1, GDP1, PMA1, MET3, CUP1, GAP, TPI, MF$\alpha$1 and MF$\alpha$2, as well as the hybrid promoters PGK/$\alpha$2, TPI/$\alpha$2, GAP/GAL, PGK/GAL, GAP/ADH2, GAP/PHO5, ADH2/PHO5, CYC1/GRE, and PGK/ARE and other promoters known in the art. Where bacterial host cells are utilized, promoters and promoter/operators such as the araB, trp, lac, gal, tac (a hybrid of the trp and lac promoter/operator), T7, and the like are useful in accordance with the instant invention. When other eukaryotic cells are the desired host cell, any promoter active in the host cell may be utilized. For example, when the desired host cell is a mammalian cell line, the promoter may be a viral promoter/enhancer (e.g., the herpes virus thymidine kinase (TK) promoter or a simian virus promoter (e.g., the SV40 early or late promoter) or the Adenovirus major late promoter, a long terminal repeat (LTR), such as the LTR from cytomegalovirus-(CMV), Rous sarcoma virus (RSV) or mouse mammary tumor virus (MMTV)) or a mammalian promoter, preferably an inducible promoter such as the metallothionein or glucocorticoid receptor promoters and the like.

Expression constructs may also include other DNA sequences appropriate for the intended host cell. For example, expression constructs for use in higher eukaryotic cell lines (e.g., vertebrate and insect cell lines) will include a poly-adenylation site and may include an intron (including signals for processing the intron), as the presence of an intron appears to increase mRNA export from the nucleus in many systems. Additionally, a secretion signal sequence operable in the host cell is normally included as part of the construct. The secretion signal sequence may be the naturally occurring ecarin signal sequence from *E. carinatus leucogaster* ecarin, or it may be derived from another gene, such as human serum albumin, human prothrombin, human tissue plasminogen activator, or preproinsulin. Where the expression construct is intended for use in a prokaryotic cell, the expression construct may include a signal sequence which directs transport of the synthesized peptide into the periplasmic space or expression may be directed intracellularly.

Preferably, the expression construct will also comprise a means for selecting for host cells which contain the expression construct (a "selectable marker"). Selectable markers are well known in the art. For example, the selectable marker may be a resistance gene, such as a antibiotic resistance gene (e.g., the $neo^r$ gene which confers resistance to the antibiotic gentamycin or the $hyg^r$ gene, which confers resistance to the antibiotic hygromycin), or it may be a gene which complements an auxotrophy of the host cell. If the host cell is a Chinese hamster ovary (CHO) cell which lacks the dihydrofolate reductase (dhfr) gene, for example CHO DUXB11 cells, a complementing dhfr gene would be preferred.

If the host cell is a yeast cell, the selectable marker is preferably a gene which complements an auxotrophy of the cell (for example, complementing genes useful in *S. cerevisiae, P. pastoris* and *S. pombe* include LEU2, TRP1, TRP1d, URA3, URA3d, HIS3, HIS4, ARG4, LEU2d), although antibiotic resistance markers such as SH BLE, which confers resistance to ZEOCIN®, may also be used. If the host cell is a prokaryotic or higher eukaryotic cell, the selectable marker is preferably an antibiotic resistance marker (e.g., $neo^r$). Alternately, a separate selectable marker gene is not included in the expression vector, and the host cells are screened for the expression of ecarin (e.g., upon induction or derepression for controllable promoters, or after transfection for a constituitive promoter, fluorescence-activated cell sorting, FACS, may be used to select those cells which express the recombinant ecarin). Preferably, the expression construct comprises a separate selectable marker gene.

The expression construct may also contain sequences which act as an "ARS" (autonomous replicating sequence) which will allow the expression construct to replicate in the host cell without being integrated into the host cell chromosome. Origins of replication for bacterial plasmids are well known. ARS for use in yeast cells are also well known (e.g., the 2μ origin of replication and operative fragments thereof) and ARS which act in higher mammalian cells have been recently described (see, for example, Pelletier et al., 1997, *J. Cell. Biochem.* 66(1):87–97). Alternately, the expression construct may be integrated into the host cell chromosome. The integration may be by random insertion, or the expression construct may include DNA sequences which will direct or allow the integration of the construct into the host cell chromosome by homologous or site-directed recombination.

Where the host cell is a eukaryotic cell, it may be advantageous for the expression vector to be a "shuttle vector", because manipulation of DNA is substantially more convenient in bacterial cells. A shuttle vector is one which carries the necessary signals for manipulation in bacteria as well as the desired host cell. So, for example, the expression construct may also comprise an ARS ("ori") which acts in prokaryotic cells as well as a selectable marker which is useful for selection of prokaryotic cells.

The host cells for use in the instant invention may be any convenient host cell, including bacterial, yeast, and eukaryotic cells. Higher eukaryotic cells are preferred host cells. For yeast host cells, *Saccharomyces cerevisiae, Pichia pastoris, Hansenula polymorpha, Kluyveromyces lactis, Schwanniomyces occidentis, Schizosaccharomyces pombe* and *Yarrowia lipolytica* strains are preferred. Of the higher eukaryotic cells, insect cells such as Sf9 are preferred, as are mammalian cell lines such as CHO, COS, 293, 293-EBNA, baby hamster kidney (BHK), HeLa, NIH/3T3, and the like.

The expression construct is introduced into the host cells by any convenient method known to the art. For example, for yeast host cells, the construct may be introduced by electroporation, lithium acetate/PEG and other methods known in the art. Higher eukaryotes may be transformed by electroporation, microprojectile bombardment, calcium phosphate transfection, lipofection, or any other method known to the art. Bacterial host cells may be transfected by electroporation, calcium chloride-mediated transfection, or any other method known in the art.

After introduction of the expression construct into the host cell, host cells comprising the expression construct are normally selected on the basis of the selectable marker that is included in the expression vector. As will be apparent, the exact details of the selection process will depend on the identity of the selectable marker. If the selectable marker is an antibiotic resistance gene, the transfected host cell population is generally cultured in the presence of an antibiotic to which resistance is conferred by the selectable marker. The antibiotic eliminates those cells which are not resistant (i.e., those cells which do not carry the resistance gene) and allows the propagation of those host cells which carry the resistance gene (and presumably carry the rest of the expression construct as well). If the selectable marker is a gene which complements an auxotrophy of the host cells, then the transfected host cell population is cultured in the absence of the compound for which the host cells are auxotrophic. Those cells which are able to propagate under these conditions carry the complementing gene to supply this compound and thus presumably carry the rest of the expression construct.

Host cells which pass the selection process may be "cloned" according to any method known in the art that is appropriate for the host cell. For microbial host cells such as yeast and bacteria, the selected cells may be plated on solid media under selection conditions, and single clones may be selected for further selection, characterization or use. Higher eukaryotic cells are generally further cloned by limiting dilution (although physical isolation methods such as micromanipulation or "cloning rings" may also be used). This process may be carried out several times to ensure the stability of the expression construct within the host cell.

For production of ecarin of the invention, the recombinant host cells comprising the expression construct are generally cultured to expand cell numbers. This expansion process may be carried out in any appropriate culturing apparatus known to the art. For yeast and bacterial cells, an apparatus as simple as a shaken culture flask may be used, although large scale culture is generally carried out in a fermenter. For insect cells, the culture is generally carried out in "spinner flasks" (culture vessels comprising a means for stirring the cells suspended in a liquid culture medium). For yeast and bacterial host cells, large scale culture is generally performed in a specially adapted apparatus, a variety of which are known in the art. Mammalian cell lines can be grown in a variety of different culture configurations, ranging from simple culture plates or flasks, to roller bottles, to more sophisticated apparati such as hollow fiber cartridges and suspended microbead systems.

The culture medium used for culture of the recombinant host cells will depend on the identity of the host cell. Culture media for the various host cells used for recombinant culture are well known in the art. The culture medium generally comprises inorganic salts and compounds, amino acids, carbohydrates, vitamins and other compounds which are either necessary for the growth of the host cells or which improve the health and/or growth of the host cells (e.g., protein growth factors and hormones where the host cells are mammalian cell lines). For the culture of mammalian host cell lines, the use of animal products (e.g., serum) is preferably avoided. Semi-defined media and defined media are preferred for use in the instant invention.

The recombinant host cells are cultured under conditions appropriate for the expression of the DNA encoding the ecarin of the invention. The exact method of inducing or derepressing the expression of the DNA encoding the ecarin of the invention will depend on the properties of the particular expression construct used and the identity of the host cell, as will be apparent to one of skill in the art. If the expression construct utilizes a controllable expression system, the expression of the DNA encoding the ecarin of the invention is induced or derepressed, as is appropriate for the particular expression construct. Generally, for inducible promoters, a molecule which induces expression is added to the culture medium. For example, for a mammalian cell line transformed with an expression vector utilizing the metallothionein promoter, a metal, such as zinc, is added to the culture medium. In bacteria utilizing an expression vector with the lac promoter, isopropyl-β-D-thiogalactopyranoside (IPTG) is added to the medium to derepress expression. For constituitive promoters, the cells are cultured in a medium providing the appropriate environment and sufficient nutrients to support the survival of the cells.

Proecarin produced according to the present invention may be purified by conventional chromatographic techniques preferably using wheat germ lectin SEPHAROSE® (Amersham Pharmacia Biotech, Piscataway, N.J.). The proecarin bound to the resin may be eluted by exposure to N-acetyl-D-glucosamine (Fortova et al., 1983, *J. Chrom.* 260:522–526). Alternatively the proecarin may be purified by immobilized metal affinity chromatography (the catalytic domain of ecarin contains a metal binding motif) using resin such as chelate SEPHAROSE® (Amersham Pharmacia Biotech, Piscataway N.J.) charged with metal ions such as zinc, nickel, cobalt and the like. Other chromatography resins such as ion exchange (Q- and SP-SEPHAROSE®), Cibacron Blue-SEPHAROSE® and various gel filtration resins will also be effective for purifying proecarin of the present invention (Rhee et al., 1982, supra; Morita et al., 1978, *J. Biochem*. 83:559–570).

Ecarin of the invention may be used for proteolytic processing of proteins containing an ecarin recognition site. The ecarin recognition site may be endogenous, as in the case of prothrombin, or it may as a result of genetic engineering (e.g., a recombinant fusion protein which has been engineered to add an ecarin recognition site). The results of proteolytic processing will, of course, depend on the identity and properties of the protein that is processed with ecarin. When the protein processed by ecarin is a fusion protein containing an ecarin recognition site at the link between the fusion partners, proteolytic processing results in liberation of the fusion partners from the fusion protein. Such processing may be desirable for the production of recombinant proteins when a fusion partner is necessary for or enhances production of the fusion protein, but is not desired in the final product. In the case of prothrombin, processing with ecarin results in the production of thrombin.

Activation of prothrombin by ecarin is well characterized, and is even the basis of certain diagnostic assays for tracking anticoagulant therapy (Dyr et al., 1983, *Thromb. Res.* 30(3) :225–234; Potzsch et al., 1997, *Thromb. Res.* 86(5): 373–383). Ecarin cleaves prothrombin to yield meizothrombin, an active intermediate which autocatalytically generates α-thrombin.

A protein containing an ecarin recognition site may be processed by simply exposing the protein to an activated ecarin of the invention. Certain ecarins of the invention are constituitively active (e.g., ecarin having the sequence of FIG. 1 with an additional change at position 170 from cysteine to serine), and so need not be activated. Another method of activating ecarin is treatment with a organomercurial such as p-aminophenylmercuric acetate (APMA). APMA dissociates the cysteine in the "cysteine switch" present in native ecarin, from a zinc ion bound to the catalytic domain (e.g., ecarin having the sequence of FIG. 1). Other agents useful for activating ecarin include, but are not limited to, organomercurials such as o-[(3-hydroxymercuri-2-methoxypropyl)carbamoyl] phenoxyacetic acid (Mersalyl), p-(hydroxymercuric) benzoate (PHMB), phenylmercuric chloride (PMC) and mercuric chloride ($HgCl_2$), as well as oxidized glutathlione/ glutatnione disulfide (GSSG), N-ethylmaleimide (NEM), 5,5'-dithiobis(2-nitrobenzoic acid) (DTNB), sodium thiocyanate (NaSCN), and sodium chlorate ($NaClO_3$).

Where the ecarin of the invention is a heterologous acfivation variant ecarin, the ecarin may be activated by treatment with the appropriate protease. For such embodiments, the heterologous activation variant is preferably activated by the selected protease (e.g., if the ecarin of the invention is engineered to contain a KEX2 site, the ecarin is preferably activated with KEX2).

A number of proteases are known to activate proenzymes having a cysteine-switch domain. Proteases which can activate cysteine-switch containing proteins including trypsin, matrix metalloproteinase-2 (MMP-2, also known as type IV collagenase), stromelysin-1 (also known as MMP-3), MMP-7 (also known as matrilysin), stromelysin-2 (also known as MMP-10), MMP-14 (also known as MT1-MMP), MMP-15 (also known as MT2-MMP), and MMP-16 (also known as MT3-MMP) may also be used to activate ecarin of the invention. Where ecarin of the invention is activated by a protease, one preferred method is by limited trypsin proteolysis, preferably using trypsin immobilized on agarose beads.

Activated ecarin of the invention may be used to activate prothrombin to form active thrombin. Prothrombin is contacted with activated ecarin, which cleaves the prothrombin to yield meizothrombin, which is further autocyatalytically processed to form thrombin, particularly α-thrombin. Reaction conditions for activating prothrombin with ecarin are well known in the art, and need not be described in detail here.

Preferably proteins are proteolytically processed with ecarin by exposing the protein to be processed to ecarin under conditions which favor the activity of ecarin, for example, 20 mM Tris-HCl pH 8.4, 0.1 M NaCl, 0.2% PEG1000. The presence of divalent cations, such as calcium, is not required.

In one preferred embodiment, the protein to be processed (e.g., prothrombin or a fusion protein containing an ecarin recognition site) is exposed to an activated ecarin of the invention in solution. In this embodiment, the protein to be processed (which may be crude, such as a cell extract, conditioned media, partially pure, or purified) is mixed in solution with an activated ecarin of the invention (which may also be crude, such as a cell extract, conditioned media, partially pure, or purified). The mixture of activated ecarin and the protein to be processed is incubated for a period of time, then may be further processed to remove the ecarin and/or purify the processed protein (e.g, activated thrombin or the desired portion of the fusion protein).

In another preferred embodiment, protein to be processed with ecarin is exposed to an immobilized activated ecarin of the invention. Generally, the ecarin is bound to an insoluble support, such as a membrane, particles (e.g., beads), or a vessel wall. Suitable insoluble supports include glass, polystyrene, polypropylene, polyethylene, dextran, nylon, amylase, natural and modified cellulose, polyacrylamide, agarose, modified agarose (e.g., crosslinked) and magnetite. Preferred supports include agarose, modified agarose (e.g., SEPHAROSE®), cellulose and modified cellulose.

The ecarin may be immobilized by a covalent linkage, such as by use of an activated support (e.g., CNBr-activated or NHS-activated) or it may be non-covalently associated. Non-covalent association is usually by means of a binding pair. For example, the ecarin may be derivatized with a molecule such as biotin, which is strongly bound by avidin and streptavidin, and so would become non-covalently bound to a support comprising avidin or streptavidin. Fusion proteins which fuse one half of a binding pair to the ecarin are also useful in this embodiment. For example, a polyhistidine "tag" may be fused to the ecarin, and bound to a metal chelating column loaded with a metal such as zinc or nickel. These and other methods for covalently and non-covalently attaching a protein of interest to a support are well known in the art, and are thus not described in detail here. The ecarin bound to the support may be activated before or after the ecarin is bound to the support.

Prothrombin or any other protein containing an ecarin recognition site may be exposed to the immobilized activated ecarin of the invention by contacting a solution containing the protein of interest (e.g., prothrombin or a protein containing an ecarin recognition site) with the immobilized activated ecarin. In some embodiments, the solution containing the ecarin recognition site-containing protein may be incubated with the immobilized activated ecarin for an extended period or, more preferably, the solution containing the ecarin recognition site-containing protein may be recirculated over or through the activated ecarin-derivatized support.

Prothrombin and other proteins containing ecarin recognition sites may also be activated to thrombin in vivo, by co-expression of prothrombin or protein containing an ecarin recognition site and an ecarin of the invention in the same host cell. Preferably the ecarin expressed is a constituitively active ecarin of the invention, although heterologous activation variant ecarins of the invention may also be used.

EXAMPLES

Example 1

Expression of Proecarin in COS Cells

Seven different constructs were created to test various parameters of ecarin. Three fusion proteins were constructed, adding a polyhistidine "tag" ($His_6$) to the carboxy terminus of the protein: preproecarin S396, pDOEC30 (e.g., the sequence of FIG. 1); preproecarin P396, pDOEC34 (e.g., the sequence disclosed by Nishida et al., supra); and preproecarin S396,S170, pDOEC35 (e.g., the sequence of FIG. 1 with residue 170 altered to a serine). An additional four deletion constructs were made, deleting either the Cys-rich domain (ΔIV) or the disintegrin and Cys-rich domains (ΔIII,IV) from preproecarin S396, pDOEC37, pDOEC38 respectively and preproecarin S396,S170, pDOEC39, and pDOEC40. All proecarin sequences described above were cloned into plasmid pSG5 (Stratagene, San Diego Calif.) which utilizes the SV40 early promoter, contains the rabbit B-globin intron immediately downstream of the promoter, and the poly A signal from SV40.

COS-7 cells were obtained from the ATCC (CRL 1651) and were maintained in DMEM supplemented with 10% FBS, glutamine 1 mg/ml, penicillin 100 units/ml, and streptomycin 100 μg/ml. Cells were maintained in culture and routinely passed 1:10. The day prior to transfection cells were plated at $2.5 \times 10^5$ cells/60 mm dish. Plasmid DNA was introduced into cells using the GenePorter transfection reagent (Gene Therapy Systems, San Diego, Calif.) as recommended by the manufacturer. Normally, 3 μg of plasmid DNA, prepared with QIAGEN Plasmid Maxi kit, was used per 60 mm dish of cells. Cells were incubated with DNA for 4 hours, allowed to recover in complete media for 24 hours, washed three times with PBS, feed with 4 ml of serum-free DMEM supplemented with insulin, selenium, and transferrin (GIBCO Life Technologies, ITS-X supplement), and allowed to grow for an additional 4 days. The conditioned media was collected, chilled to 4° C. and cell debris was removed by centrifugation. Proecarin in the media was activated by treatment with 1 mM APMA dissolved in 50 mM NaOH, in the presence of 0.1 M Tris-HCl pH 8.0, for 1 hour at 37° C. Media (15 μl) was assayed for prothrombin converting activity by incubating 10 μg of purified human prothrombin in 20 mM Tris-HCl pH 8.4, 0.1 M NaCl, 0.2% PEG1000 for 2 hours at 37° C. Aliquots of these reaction mixtures were analyzed on 4–20% gradient gels (Novex, San Diego, Calif.) under reducing conditions and proteins were visualized by staining with Coomassie Blue. Other aliquots were assayed for thrombin enzymatic activity using substrate S-2238 (Chromogenix-Instrumentation Laboratory SpA, Milano, Italy) in the standard chromogenic assay (Axelsson, G., et al., 1976, *Thromb. Haemost.* 36:517).

Proecarin having the sequence disclosed in Nishida et al. (supra) had no activity in the presence or absence of APMA. Proecarin having a serine at position 396 was active in the absence of APMA, and the amount of activity increased several fold by pretreatment with APMA. Alteration of position 170 to serine resulted in constituitive activation of proecarin, which was partially inhibited by the addition of APMA. Deletion of the Cys-rich domain (positions 491 to 616) or the disintegrin and Cys-rich domains (398–616) abolished all ecarin activity in the presence or absence of APMA. Results are shown in Table 1 and FIG. 3.

TABLE 1

| Construct | Ecarin Activity | | | |
|---|---|---|---|---|
| | 48 Hours | | 120 Hours | |
| | −APMA | +APMA | −APMA | +APMA |
| Control | 0 | 0 | 0 | 0 |
| preproecarin S396, $His_6$ | 20,079 | 74,077 | 28,372 | 164,602 |
| preproecarin P396, $His_6$ | 36 | 32 | 43 | 0 |
| preproecarin S396, S170, $His_6$ | 12,127 | 7,526 | 20,524 | 14,850 |
| preproecarin S396, ΔIV | 0 | 0 | 34 | 68 |
| preproecarin S396, S170, ΔIV | 0 | 0 | 0 | 0 |
| preproecarin S396, ΔIII, IV | 0 | 0 | 0 | 14 |
| preproecarin S396, S170 ΔIII, IV | 0 | 50 | 0 | 0 |

Example 2

Co-expression of Prothrombin and Proecarin in CHO Cells

A CHO cell line that overexpresses human prothrombin, designated 68.1.23.2B5, was used as the host cell for transfection of the proecarin gene. The cDNAs encoding preproecarin S396 and preproecarin S396,S170 were cloned into plasmid pSecTag2 (Invitrogen, San Diego, Calif.) following the removal of the Ig kappa secretion signal, creating plasmids pDOEC16 and pDOEC21 respectively. These constructs contain the SH BLE gene allowing transfected cells to grow in the presence of ZEOCIN®. Cell line 68.1.23.2B5 was plated at $2.5 \times 10^5$ cells/60 mm dish and transfected with 10 μg of ScaI linearized pDOEC 16, encoding preproecarin S396 (i.e., the amino acid sequence shown in FIG. 1), pDOEC21, encoding preproecarin S396, S170 (i.e., the amino acid sequence shown in FIG. 1 except that the cysteine at position 170 has been altered to serine), or pSecTag2. Forty-eight hours after transfection the cells were passaged (~1:10) and grown in media containing 400 μg/ml ZEOCIN®. After two weeks of selection, ZEOCIN®-resistant cells were passaged and maintained as a pool. Cultures that were ~75% confluent were incubated in serum-free media for 72 hours. The media was collected, centrifuged to remove cells, concentrated using a Centricon-10 spin concentrator and assayed for thrombin by Western blotting and enzymatic activity using the chromogenic assay described above, before and after treatment with APMA.

Figure 4:
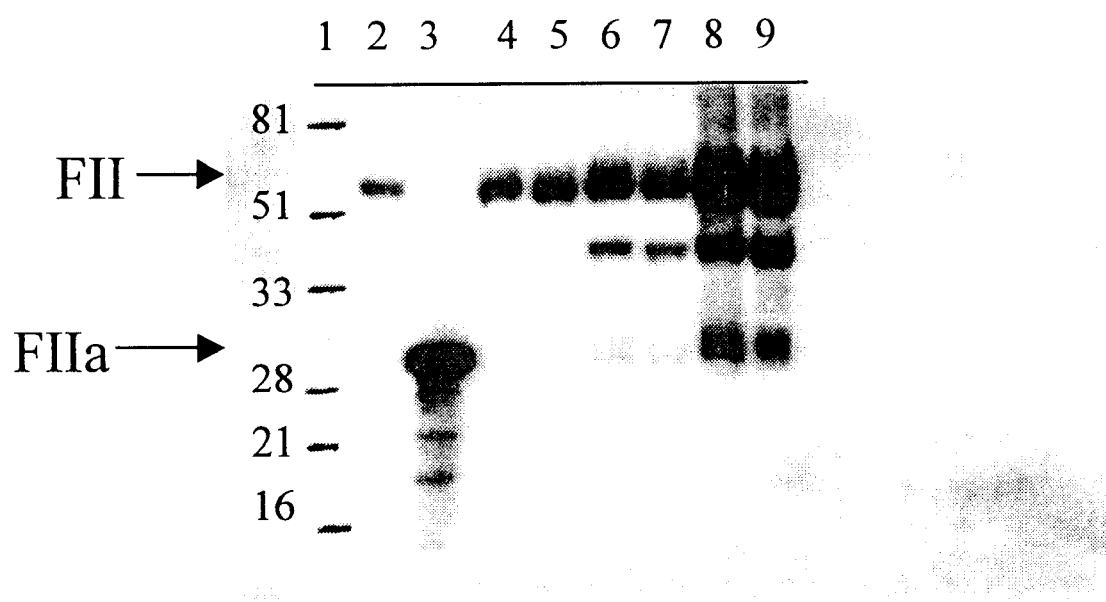
FIG. 4 shows a half-tone reproduction of a western blot demonstrating the presence of α-thrombin in the media of a CHO cell line co-expressing prothrombin and proecarin. Conditioned medium from 68.1.23.2B5 cells (DUXB11 CHO cells which overexpress human prothrombin) transfected with a control plasmid (pSECTAG, the backbone plasmid used for the other constructs; lanes 4–5), pDOEC16 (encoding the proecarin of FIG. 1 (SEQ ID NO:1); lanes 6–7), or pDOEC21 (encoding proecarin of FIG. 1 (SEQ ID NO:1) with position 170 altered to serine, lanes 8–9) was run on a 4–20% SDS-PAGE gradient gel, then transferred and blotted with an anti-thrombin antibody. Lane 1 is molecular weight markers, Lane 2 is prothrombin (untreated), lane 3 is prothrombin treated with venom-derived ecarin. Lanes 5, 7, and 9 are conditioned medium samples preincubated with APMA, while lanes 4, 6 and 8 are untreated. "FIIa" indicates the position of prothrombin and "FIIa" indicates the position of activated thrombin (α-thrombin).

No thrombin enzymatic activity could be detected in the media of either of the 3 cell lines before or after APMA treatment. Analysis of the media proteins by western blotting revealed a protein that co-migrated with the α-thrombin standard and reacted with a thrombin antibody (Affinity Biologics, Inc.) (FIG. 4). This protein was found only in the cell lines transfected with the proecarin plasmids and not in the cells transfected with the control vector. APMA treatment of the media proteins did not alter the intensity of the thrombin immunoreactive protein.

Figure 5:
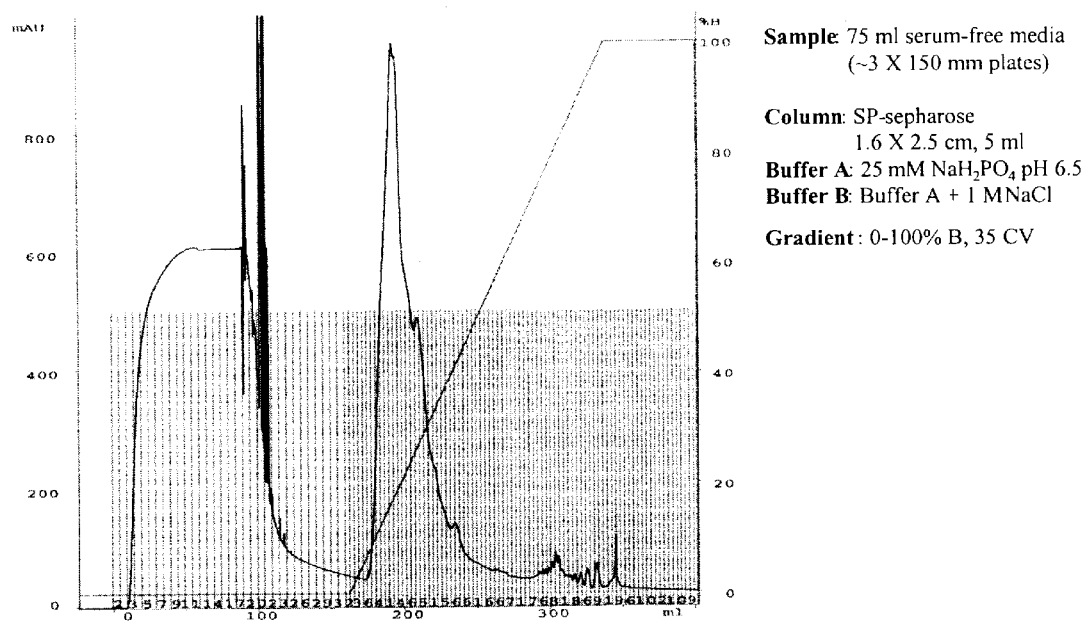
FIG. 5 shows a chromatogram from a SP-SEPHAROSE® column following fractionation of conditioned media from a CHO cell line co-expressing prothrombin and proecarin S396, S170 of the invention.
Figure 6:
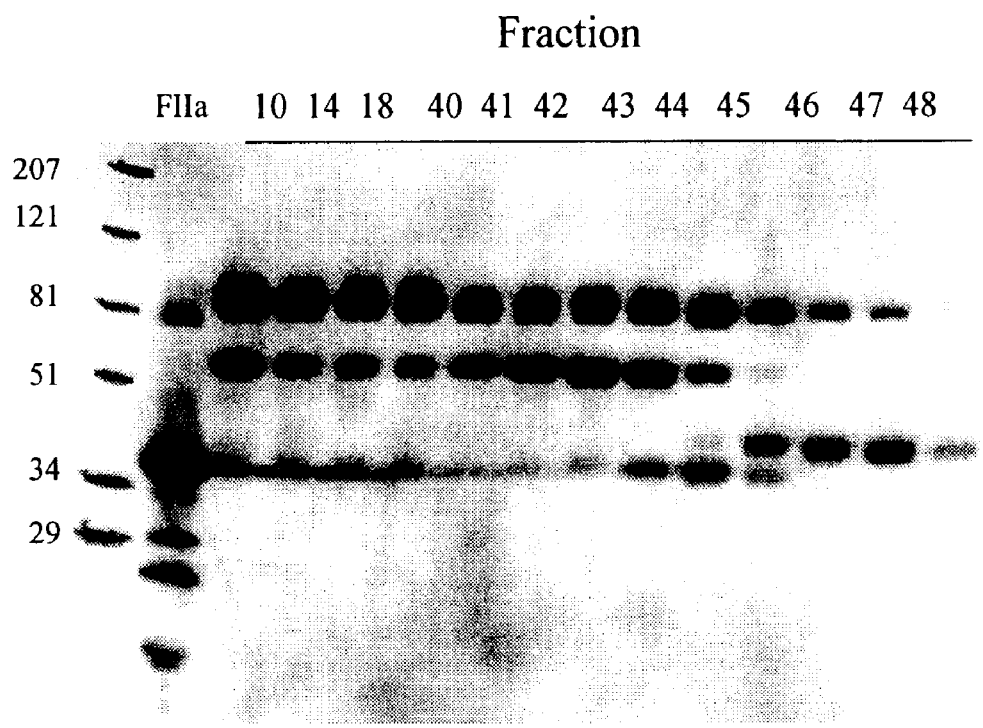
FIG. 6 shows a half-tone reproduction of western blot analysis of fractions from the SP-SEPHAROSE® column shown in FIG. 4 identifying the elution position of α-thrombin. The lane marked "FIIa" shows activated thrombin.

The detection of thrombin by western blotting suggested that co-expression of prothrombin and proecarin in the same cell can result in the generation of alpha thrombin in the conditioned media. Enzymatically active thrombin was isolated from condition medium from three 150 mm cultures of CHO cells co-expressing prothrombin and preproecarin S396, S170 (72 hour incubation). The media was collected, centrifuged to remove any cells and debris, dialyzed into 25 mM sodium phosphate buffer pH 6.5 and was run on a 5 ml SP-SEPHAROSE® column to purify and concentrate the thrombin. Bound proteins were eluted with a 0–1.0 M NaCl gradient over 35 column volumes (FIG. 5). Western blot and activity assays were performed on the fractions from the cation exchange column. Fractions 43–45 which eluted from the column during the NaCl gradient were found to contain thrombin immunoreactive protein (FIG. 6) and those same fractions also contained thrombin enzymatic activity (Table 2). Thrombin immunoreactive protein was also detected in several of the column flow through fractions, barely detectable activity was associated with those fractions.

TABLE 2

| Fraction | Absorbance (units/min) |
|---|---|
| Load | 2.1 |
| 2 | 0.0 |
| 4 | 0.15 |
| 6 | 0.0 |
| 8 | 0.37 |
| 10 | 0.41 |
| 12 | 2 |
| 18 | 0.6 |
| 20 | 0.39 |
| 40 | 0.70 |
| 42 | 4.06 |
| 44 | 18.33 |

TABLE 2-continued

| Fraction | Absorbance (units/min) |
|---|---|
| 46 | 1.04 |
| 48 | 0.41 |

These results indicate that co-expression of ecarin and prothrombin results in the production of active thrombin.

Example 3

Activation of Prothrombin with Immobilized Ecarin

Conditioned media from COS-7 cells transfected with plasmid pDOEC30 was collected as described in Example 1, and concentrated 8-fold using a stirred cell concentrator with a 30,000 Dalton molecular weight cut off membrane. The concentrated media was incubated with 1 mM APMA for 16 hours to activate proecarin and then dialyzed into 0.1 M $NaH_2PO_4$ pH 7.0, 0.5 M NaCl, 10 mM imidazole (Buffer A). The sample was then run on a 1 ml chelate-SEPHAROSE® (Pharmacia) column that had been charged with $Ni^{+2}$ and equilibrated in Buffer A. The column was washed extensively with Buffer A, then equilibrated in 20 mM Tris-HCl pH 8.4, 0.1 M NaCl, 0.2% PEG (Buffer B) to maintain the proecarin immobilized on the column and prepare it for reaction with prothrombin. A 5 ml solution containing 2 mg of recombinant human prothrombin in Buffer B was circulated through the column containing the immobilized proecarin for 16 hours at room temperature at a flow rate of 0.2 ml/minute. The column eluate was collected and analyzed by SDS-PAGE gel to visualize the reaction products and assayed for thrombin activity.

Figure 7:
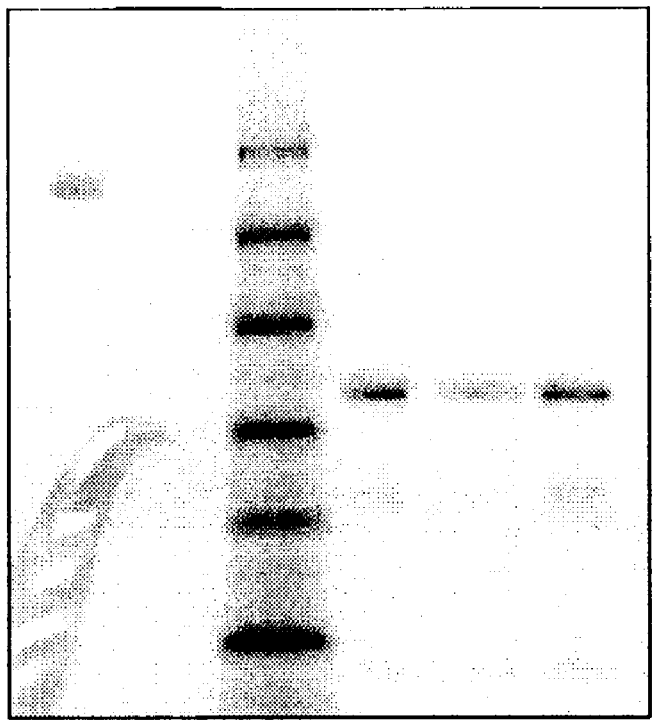
FIG. 7 shows SDS-PAGE analysis of prothrombin before and after circulation through a column of immobilized ecarin of the invention. Lane 1 is purified prothrombin. Lane 2 is molecular weight markers. Lane 3 is prothrombin activated by incubation in solution with ecarin at room temperature (approximately 20° C.). Lane 4 is prothrombin a activated by incubation in solution with ecarin at 37° C. Lane 5 is prothrombin activated by recirculation over an ecarin-derivatized column. Protein was visualized by staining with Coomassie blue.

The eluate contained active thrombin, based on the chromogenic assay and the conversion of prothrombin to thrombin was essentially complete (greater than 95%) based on the Coomassie stained protein profile (FIG. 7).

We claim:

1. An isolated ecarin prothrombin protease comprising a catalytic domain having a sequence at least 85% identical to amino acids 191–397 of SEQ ID NO:1 and having a serine at a position corresponding to amino acid 396 of SEQ ID NO:1, wherein said protease cleaves prothrombin.

2. The protease of claim 1, wherein the sequence identity is at least 90%.

3. The protease of claim 1, wherein the sequence identity is at least 95%.

4. The protease of claim 1, wherein the sequence identity is at least 99%.

5. The protease of claim 1, wherein the sequence identity is 100%.

6. The protease of claim 1, comprising a sequence at least 85% identical to amino acids 191–616 of SEQ ID NO:1.

7. The protease of claim 1, comprising amino acids 191–616 of SEQ ID NO:1.

8. The protease of claim 1, comprising a sequence at least 85% identical to amino acids 19–616 of SEQ ID NO:1.

9. The protease of claim 1, comprising amino acids 19–616 of SEQ ID NO:1.

10. The protease of claim 1, comprising SEQ ID NO:1.

11. The protease of claim 1 which further comprises a recognition and cleavage site for a protease which does not normally cleave proecarin.

12. The protease of claim 1 which further comprises a recognition and cleavage site for a protease which does not normally cleave proecarin, wherein said cleavage site is located immediately prior to a position corresponding to amino acid 191 of SEQ ID NO:1.

13. The protease of claim 1 comprising a cysteine to serine substitution at position 170, wherein said substitution functionally inhibits a cysteine switch at a position corresponding to amino acid 170 of SEQ ID NO:1.

14. A method of producing an ecarin prothrombin protease, the method comprising culturing a cell to express the protease of claim 1 and isolating the protease.

15. A method of producing an ecarin prothrombin protease, the method comprising culturing a cell to express the protease of claim 5 and isolating the protease.

16. A method of producing an ecarin prothrombin protease, the method comprising culturing a cell to express the protease of claim 6 and isolating the protease.

17. A method of producing an ecarin prothrombin protease, the method comprising culturing a cell to express the protease of claim 7 and isolating the protease.

18. A method of producing an ecarin prothrombin protease, the method comprising culturing a cell to express the protease of claim 9 and isolating the protease.

19. A method for proteolytically processing a protein comprising an ecarin recognition site, comprising contacting a protein containing an ecarin recognition site with the protease of claim 1 whereby the protein is proteolytically processed at the ecarin recognition site.

20. A method for proteolytically processing a protein comprising an ecarin recognition site, comprising contacting a protein containing an ecarin recognition site with the protease of claim 5 whereby the protein is proteolytically processed at the ecarin recognition site.

21. A method for proteolytically processing a protein comprising an ecarin recognition site, comprising contacting a protein containing an ecarin recognition site with the protease of claim 6, whereby the protein is proteolytically processed at the ecarin recognition site.

22. A method for proteolytically processing a protein comprising an ecarin recognition site, comprising contacting a protein containing an ecarin recognition site with the protease of claim 7, whereby the protein is proteolytically processed at the ecarin recognition site.

23. A method for proteolytically processing a protein comprising an ecarin recognition site, comprising contacting a protein containing an ecarin recognition site with the protease of claim 9, whereby the protein is proteolytically processed at the ecarin recognition site.

24. The method of claim 19, wherein said protein is prothrombin.

25. The method of claim 20, wherein said protein is prothrombin.

26. The method of claim 21, wherein said protein is prothrombin.

27. The method of claim 22, wherein said protein is prothrombin.

28. The method of claim 23, wherein said protein is prothrombin.

* * * * *